United States Patent [19]

Kowalewski

[11] Patent Number: 4,856,510
[45] Date of Patent: Aug. 15, 1989

[54] TRACHEAL TUBE INFLATOR

[76] Inventor: Ryszard J. Kowalewski, 39 Delaronde Terrace, Saskatoon, Saskatchewan, Canada, S7J 3Y9

[21] Appl. No.: 178,312

[22] Filed: Apr. 6, 1988

[51] Int. Cl.[4] .................... A61M 16/00; A61M 25/00; A61M 7/00
[52] U.S. Cl. .......................... 128/207.15; 128/207.14; 604/98; 604/100
[58] Field of Search .................. 417/394; 138/93; 128/911, 912, 207.14, 207.15, 207.16; 604/97, 98, 100, 99, 102

[56] References Cited

U.S. PATENT DOCUMENTS

| | | | |
|---|---|---|---|
| 1,852,242 | 4/1932 | Holt | 417/394 |
| 2,291,912 | 8/1942 | Myers | 417/394 |
| 3,543,758 | 12/1970 | McWhorter | 604/100 |
| 3,675,658 | 7/1972 | Taylor | 604/98 |
| 3,818,903 | 6/1974 | Bleecker | 604/98 |
| 3,901,246 | 8/1975 | Wallace | 128/207.15 |
| 4,064,882 | 12/1977 | Johnson et al. | 128/207.15 |
| 4,315,512 | 2/1982 | Fogarty | 604/97 |
| 4,423,725 | 1/1984 | Baran et al. | 128/207.15 |
| 4,617,015 | 10/1986 | Foltz | 604/100 |
| 4,637,588 | 1/1987 | Wilhelm et al. | 138/93 |
| 4,649,914 | 3/1987 | Kowalewski | 128/207.15 |
| 4,685,457 | 8/1987 | Donenfeld | 128/207.14 |

FOREIGN PATENT DOCUMENTS

| | | | |
|---|---|---|---|
| 0971457 | 7/1975 | Canada | 604/99 |
| 0064653 | 11/1982 | European Pat. Off. | 138/93 |
| 2441074 | 7/1980 | France | 417/394 |
| 0199338 | 12/1967 | U.S.S.R. | 128/207.15 |
| 0685295 | 9/1979 | U.S.S.R. | 128/207.15 |
| 0963503 | 10/1982 | U.S.S.R. | 128/207.14 |

Primary Examiner—Edgar S. Burr
Assistant Examiner—Kimberly L. Asher
Attorney, Agent, or Firm—Murray E. Thrift; Stanley G. Ade; Adrian D. Battison

[57] ABSTRACT

A tracheal tube assembly has a tracheal tube carrying an inflatable cuff and an inflation tube for the cuff. A novel inflator for the cuff has serially avenged pilot and control balloons, with the control balloon having a higher compliance than the pilot balloon and being connected directly to the inflation tube. Inlet and outlet valves are mounted in a support tube extending through the pilot balloon and into the control balloon. Both valves are check valves, open by pressing a pin on the valve element. To open the outlet valve, an opening head is resiliently connected to the end of the support tube inside the control balloon.

17 Claims, 4 Drawing Sheets

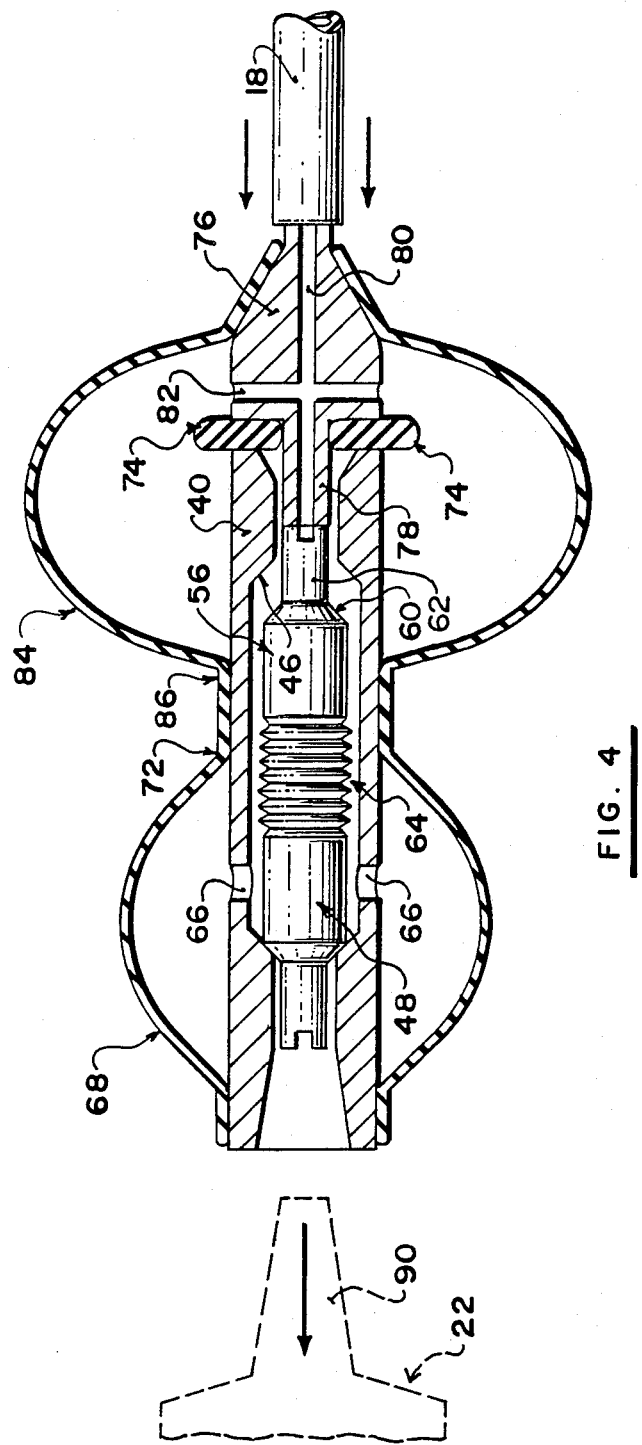

TRACHEAL TUBE INFLATOR

FIELD OF THE INVENTION

The present invention relates to new and useful improvements in tracheal tube assemblies, and in particularly to the inflators thereof.

BACKGROUND

A tracheal tube is a medical device commonly used in intensive care and during operations under general anesthesia. It consists of a flexible tube with the distal end surrounded by a cuff. When inserted into the trachea, inflation of this cuff seals the tube to the tracheal wall. This facilitates ventilation and also secures the patient's airway from aspiration of gastric contents and other foreign material.

Conventionally, air or other fluid is injected into the tracheal cuff by means of an inflation syringe attached to a pilot balloon. This system has many inherent disadvantages. Manual inflation by syringe is inconvenient, sometimes requires the assistance of a second party and delays the inflation of the cuff. It is especially important to protect the patient's airway when the risk of aspiration of gastric contents is high, as in anaesthesia for caesarean section, traumatized patients and operations for acute abdominal conditions. It is in these situations that a system is especially indicated which provides rapid and non-manual inflation of the tracheal cuff, eliminating time delay and need for assistance during intubation of the trachea.

Over compression of the tracheal mucosa by the inflated cuff is another problem with the conventional tracheal tube inflator. The pressure of the tracheal cuff can only be estimated crudely by palpation of the pilot balloon. With manual inflation, the tracheal cuff pressure may frequently exceed the desired pressure of approximately 20 mm Hg. In addition, during general anaesthesia with nitrous oxide, diffusion of nitrous oxide into the tracheal cuff will increase the pressure exerted on the tracheal wall. This results in a high incidence of complications such as sore throat, hoarseness and tracheal damage after removal of the tube. To prevent this, the cuff pressure must be checked and adjusted frequently. This is inconvenient and time consuming and seldom done in practice.

These problems are addressed in the applicant's U.S. patent 4,649,914 which describes an inflator for a tracheal cuff that includes an inner flexible balloon surrounded by an outer balloon of higher compliance. At the upstream end of the inner balloon is an inflation/deflation valve. A control valve is connected to the downstream end of both balloons and to an inflating tube for the tracheal cuff to pass pressurized air from the inner balloon to the inflating tube and to connect the inflating tube to the outer control balloon.

In use, the inner balloon is inflated or "preloaded" through the upstream valve. At the appropriate moment, the downstream valve is opened to cause rapid inflation of the cuff. The outer balloon then acts in concert with the cuff to maintain substantially constant pressure in the cuff.

The present invention is concerned with the provision of improved inflator configurations for this purpose.

SUMMARY OF THE INVENTION

According to one aspect of the present invention there is provided a tracheal tube inflator comprising:
an inflatable pilot balloon with an inlet and an outlet;
a selectively openable inlet valve connected to the inlet of the pilot balloon;
a selectively openable outlet valve connected to the outlet of the pilot balloon;
an inflatable control balloon of substantially higher compliance than the pilot balloon and having an inlet secured to the outlet valve and an outlet adapted for connection to an inflating tube for a tracheal cuff.

The separation of the pilot and control balloons in a serial arrangement provides a much more easily manufactured and monitored system. The connection between the control balloon and the inflator valve is no longer valved, so that it cannot be inadvertently closed.

According to another aspect of the present invention there is provided a tracheal tube inflator comprising:
a support tube having an inlet valve seat adjacent one end, an outlet valve seat adjacent the other end and at least one opening in the tube between the valve seats;
inlet and outlet valve elements in the tube, between the valve seats and comprising respective valve heads engagable with the respective valve seats and biasing means biasing the valve heads into engagement with the respective valve seats;
a pilot balloon surrounding a portion of the tube with inlet and outlet openings secured to the tube on opposite sides of the at least one opening therein; and
a control balloon higher in compliance than the pilot balloon with an inlet secured to the tube downstream of the pilot balloon and an outlet adapted for connection to a tracheal cuff inflating tube.

The use of a support tube containing the valves is a particularly effective arrangement from both the manufacturing and use points of view. In preferred embodiments of this sort, a valve opening head is connected to the downstream end of the support tube through a resilient connection so that in order to open the outlet valve, to inflate the cuff and the control balloon, the opening head is pushed towards the outlet end of the support tube to lift the outlet valve off its valve seat. This manipulation is particularly easy where the valve opening head is connected to the end of the inflation tube so it is simply a matter of compressing the complete assembly from end to end in order to charge the cuff and the control balloon.

The invention further provides tracheal tube assemblies including the inflators.

BRIEF DESCRIPTION OF DRAWINGS

In the accompanying drawings which illustrate exemplary embodiments of the present inventions:

FIG. 4 is a view like FIGS. 2 and 3 illustrating the inflation of the tracheal cuff and the control balloon.

DETAILED DESCRIPTION

Figure 1:
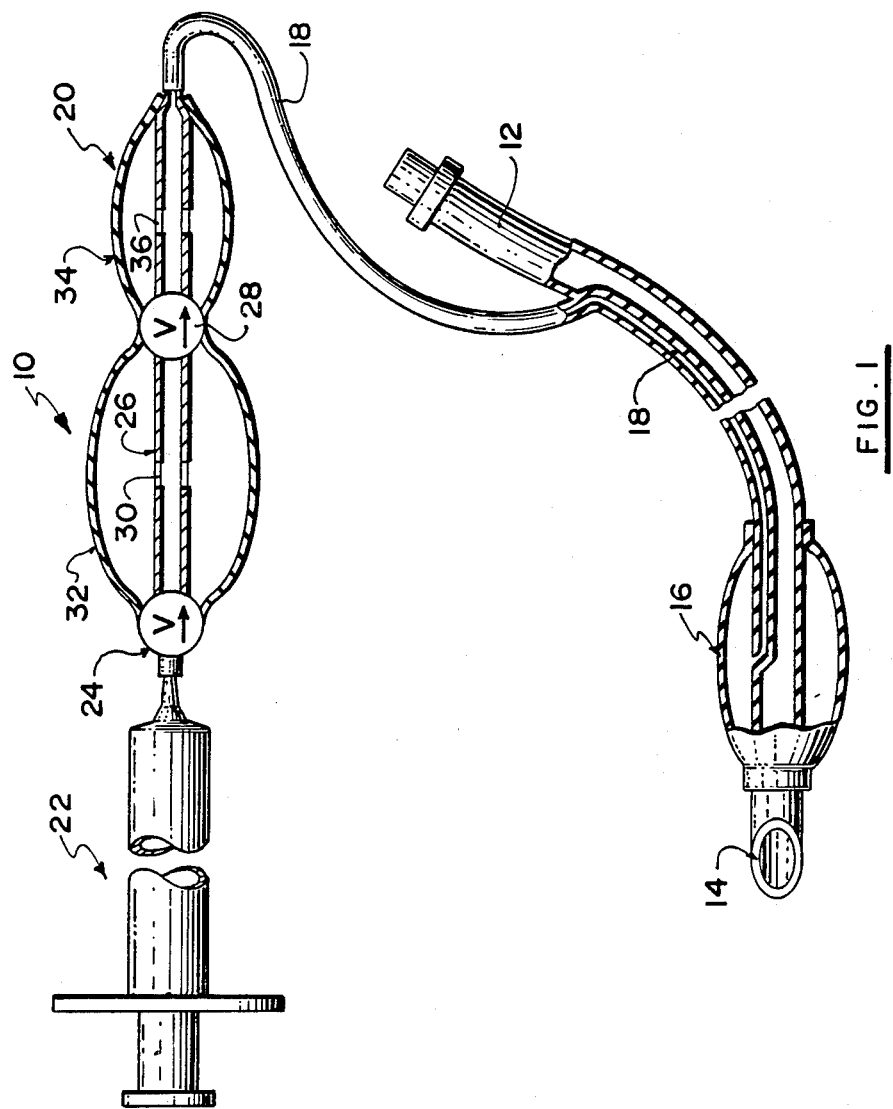
FIG. 1 is a schematic representation of a tracheal tube assembly according to the present invention.

Referring to the accompanying drawings, and particularly to FIG. 1, there is illustrated a tracheal tube assembly 10. This includes a flexible tracheal tube 12 the distal end 14 of which is intended to be introduced to the trachea of a patient. An inflatable cuff 16 is secured to the tube 12 adjacent its distal end and communicates with an inflation tube 18 integral with the wall of the tracheal tube at least part way to the proximal end where the tube becomes an independent element leading to an inflator assembly 20. The tracheal tube assembly is completed by an inflating syringe that is used for injecting air to inflate the cuff 16.

As illustrated in FIG. 1, the inflator 20 includes an inlet check valve 24 adjacent the syringe 22. This is connected to a support tube 26 that extends the length of the inflator and connects at its downstream end to the inflation tube 18. Part way along its length, the support tube is provided with a second check valve 28 that is used as an outlet check valve as described in the following.

Openings 30 in the support tube 26 between the check valves lead to the interior of a pilot balloon 32 that surrounds the support tube between the check valves and is secured at its opposite ends to the valves. Downstream of the check valve 28 is a control balloon 34 of high compliance connected to the valve 28 and to the end of the support tube adjacent its connection of the inflation tube 18. Openings 36 in the tube downstream of the check valve 28 lead into the interior of the control balloon 34.

In use of this embodiment of the device, the syringe is used to pump air through the check valve 24 and into the pilot balloon 32, which becomes inflated. At this time, the tracheal cuff 16 is deflated so that the tube 12 may be introduced into the trachea of a patient. When it is desired to inflate the cuff 16, the check valve 28 is opened and air is discharged from the pilot balloon, through the support tube 26 into the inflation tube 18 and the control balloon 34. The cuff 16 and the control balloon are thus inflated.

As noted above, the control balloon has a high compliance and thus expands readily with very little increase in internal pressure. The result is that the pressure within the control balloon and the tracheal cuff remain fairly constant regardless of the amount of air introduced from the pilot balloon on opening of the check valve 28 and regardless of any other factors that may cause the volume of gas in the combined control balloon and cuff system to change.

Figure 2:
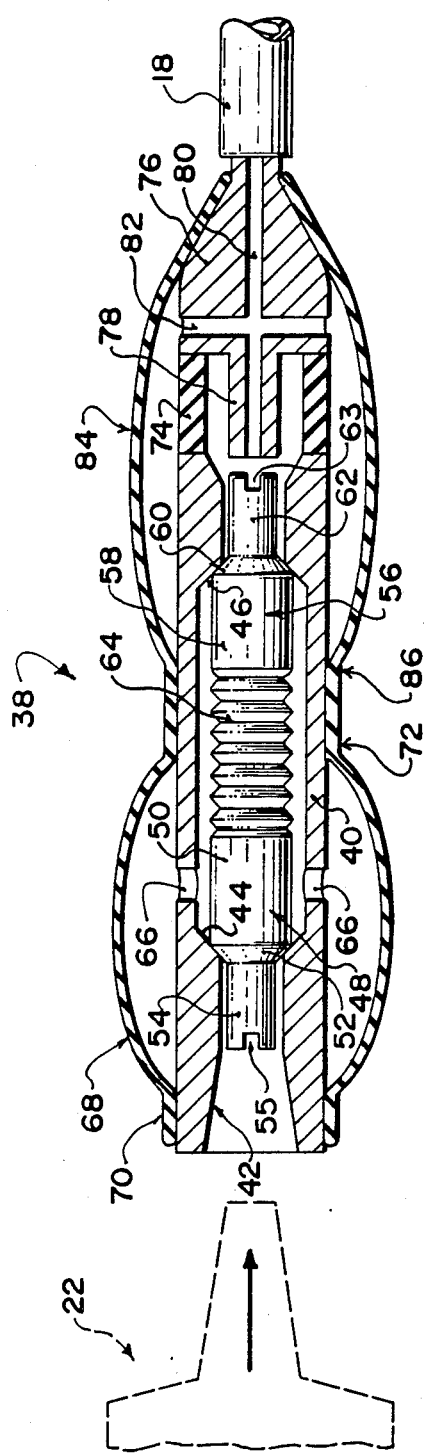
FIG. 2 is a side elevation of the inflator for the tracheal tube assembly in its condition ready for use.
Figure 3:
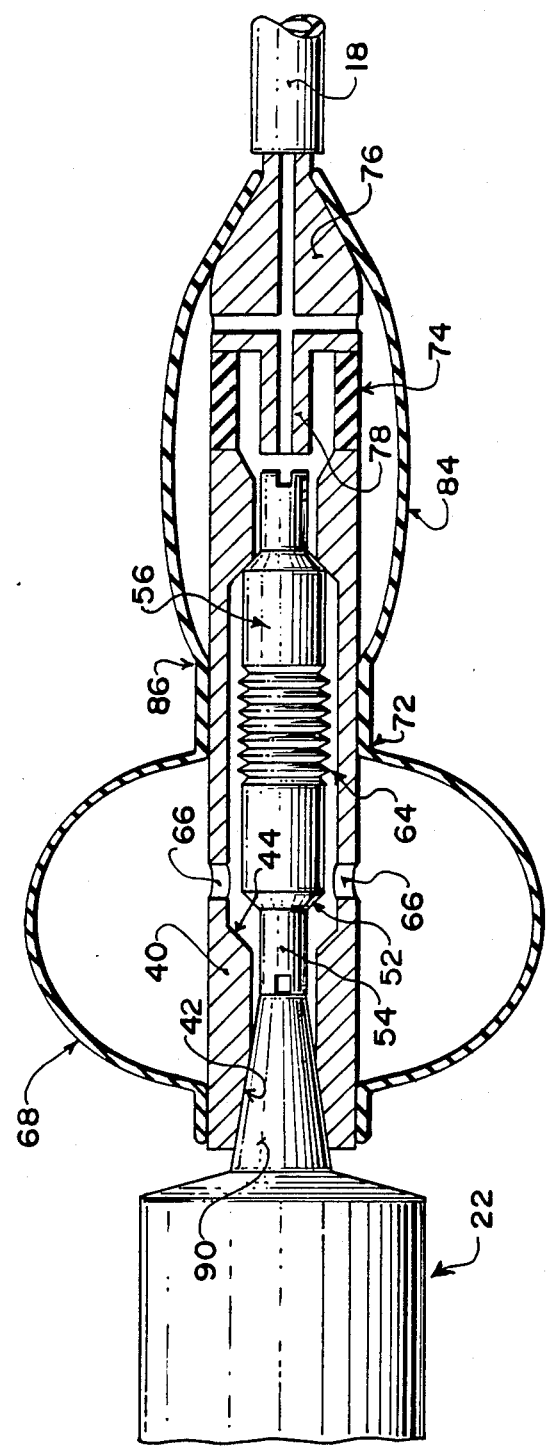
FIG. 3 is a view like FIG. 2 showing the inflation of the pilot balloon.

FIGS. 2 through 4 illustrate a preferred form of inflator 38. This consists of a support tube 40 with a frusto-conical syringe seat 42 at the inlet end. An oppositely directed frusto-conical inlet valve seat 44 is located inwardly of the syringe seat 42 and a similar frusto-conical seat 46 confronts the valve seat 44 adjacent the opposite end of the tube. An inlet valve element 48 has a cylindrical body 50, a conical end face 52 that engages the valve seat 44 and a pin 54 that projects beyond the valve seat and into the space bounded by the syringe seat 42. A diametric slot 55 is formed in the end of the pin 54.

An outlet valve 56 configured much like the inlet valve has a cylindrical body 58, a conical end face 60 that engages the valve seat 46 and a pin 62 that projects through the valve seat towards the outlet end of the support tube 40. A diametric slot 63 is formed in the end of the pin 62. A rod of resilient material 64 engages the inner face of each of the valve elements 48 and 56 to bias the two valve elements into their respective valve seats 44 and 46, thus closing both valves.

A pair of openings 66 in the tube 40 leads from the interior of the tube, between the valve seats, to the inside of a pilot balloon 68 that surrounds the tube adjacent the inlet end. An inlet end 70 and an outlet 72 of the pilot balloon are sealed to the support tube 40.

Downstream of the support tube 40 is a resilient cylinder 74 that is secured to the downstream end of the tube and the upstream end of a valve opener 76. The valve opener is a block of material with a hollow pin 78 projecting from its upstream end, into a position where it confronts the end of the valve pin 62. An axial bore 80 through the pin 78 and the body of the valve opener 76 is used an an outlet opening for connection to the inflation tube of a tracheal cuff. A cross bore 82 in the valve opener 76 provides communication between the bore 80 and the interior of a control balloon 84 surrounding the downstream end of the support tube 40 and the valve opener 76. One end 86 of the control balloon is sealed to the support tube 40, while the other end is sealed to the valve opener.

As illustrated in FIG. 2, the inflator is in the at rest position, with both valves closed. Before use, the pilot balloon 68 is preloaded, as illustrated in FIG. 3, by the introduction of a syringe tip 90 into the syringe seat 42 to engage the pin 54 and lift the valve element 48 from its valve seat. The syringe is then operated to pump air into the pilot balloon, through the support tube 40 and the openings 66. The outlet valve element 56 remains firmly engaged with its valve seat 46 so that all air pumped into the inflator is retained in the pilot balloon.

To release the air from the pilot balloon into the control balloon and the tracheal cuff, the valve opener 76 is pressed towards the end of the support tube 40, compressing the resilient cylinder 74 and bringing the pin 78 into engagement with the pin 62 of the outlet valve element 56. This lifts the outlet valve off its seat 46 so that air in the pilot balloon may pass through the openings 66 into tube 40, through the open outlet valve, into the bore 80 of the valve opener and thence to the inflation tube for the cuff and, through the cross bore 82, into the control balloon. On release of the valve opener, the outlet valve closes once more, isolating the pilot balloon from the constant pressure system consisting of the control balloon, the tracheal cuff and the adjoining inflation tube.

While FIG. 4 shows the syringe removed from the syringe seat 42 of the inflator, it may remain in place without detrimental effect. Both the syringe itself and the outlet valve serve to seal the inflator against leakage.

While particular embodiments of the invention have been described in the foregoing, it is to be understood that other embodiments are possible within the scope of the present invention. Thus, the two check valves may take widely varying forms and may be independent or coupled through the use of a common biasing means and a common support means. The common biasing means, where employed may be a resilient rod, like rod 64, integral with the valve element. In some embodiments, the support tube may be omitted although the supporting function that it provides is presently considered to be an advantage. It is also possible, and can be in many cases desirable, to provide an outer protective cover for one or both of the balloons.

I claim:

1. A tracheal tube inflator comprising:
an inflatable pilot balloon with an inlet and an outlet;

a selectively openable inlet valve connected to the inlet of the pilot balloon;

a selectively openable outlet valve connected to the outlet of the pilot balloon the outlet valve being a check valve comprising a valve body, a valving element reciprocable in the valve body between a valve closed position and a valve open position, and means for biasing the valving element to the valve closed position;

an inflatable control balloon of substantially higher compliance than the pilot balloon and having an inlet secured to the outlet valve and an outlet adapted for connection to an inflating tube for a tracheal cuff; and means within the control balloon for moving the valving element of the outlet valve to the valve open position.

2. An inflator according to claim 1 wherein the inlet valve is a check valve.

3. An inflator according to claim 2 wherein the inlet valve comprises a valve body and a valve element reciprocable therein between a normal valve closed position and a valve open position, and a means for biasing the valve element into the valve closed position.

4. A tracheal tube inflator comprising:

a rigid support tube;

an inflatable pilot balloon surrounding at least a portion of the support tube with inlet and outlet openings secured to the tube;

selectively openable inlet and outlet valves carried by the support tube adjacent the inlet and outlet respectively of the pilot balloon;

at least one opening in the support tube between the inlet and the outlet valves; and an inflatable control balloon of substantially higher compliance than the pilot balloon and having an inlet secured to the outlet valve and an outlet adapted for connection to an inflating tube for a tracheal cuff.

5. A tracheal tube inflator comprising:

a support tube having an inlet valve seat adjacent one end, an outlet valve seat adjacent the other end and at least one opening in the tube between the valve seats;

inlet and outlet valve elements in the tube, between the valve seats and comprising respective valve heads engagable with the respective valve seats and biasing means biasing the valve heads into engagement with the respective valve seats;

a pilot balloon surrounding a portion of the tube with inlet and outlet openings secured to the tube on opposite sides of the at least one opening therein; and a control balloon higher in compliance than the pilot balloon with an inlet secured to the tube downstream of the pilot balloon and an outlet adapted for connection to a tracheal cuff inflating tube.

6. A tracheal tube inflator comprising:

a support tube having an inlet valve seat adjacent one end, an outlet valve seat adjacent the other end and at least one opening in the tube between the valve seats;

inlet and outlet valve elements in the tube, between the valve seats and comprising respective valve heads engagable with the respective valve seats and biasing means biasing the valve heads into engagement with the respective valve seats;

a pilot ballon surrounding a portion of the tube with nlet and outlet openings secured to the tube on opposite sides of at least one opening therein;

a control balloon higher in compliance than the pilot balloon with an inlet secured to the tube down stream of the pilot balloon and an outlet adapted for connection to a tracheal cuff inflating tube; and valve opening means within the control balloon for selectively opening the outlet valve.

7. An inflator according to claim 6 wherein the valve opening means comprise an opening head with a valve opening pin thereon, adapted to engage the outlet valve head and to lift it from the associated valve seat.

8. An inflator according to claim 7 including compressible elastic means connecting the opening head to the adjacent end of the support tube.

9. An inflator according to claim 8 wherein the control balloon is secured to the opening head.

10. An inflator according to claim 9 wherein the opening head is secured to the inflating tube.

11. An inflator according to claim 5 wherein the biasing means comprise a resilient element extending between said valve elements and biasing them apart, into engagement with the respective valve seats.

12. An inflator according to claim 11 wherein the resilient element is integral with the valve elements.

13. A tracheal tube assembly comprising a tracheal tube, an inflatable cuff on said tube, an inflation tube leading from the cuff, at least partially along the tracheal tube, and a cuff inflator, connected to the inflation tube, said cuff inflator comprising:

a rigid support tube with spaced, opposed inlet and outlet valves therein, and an opening between the valves;

a pilot balloon surrounding the support tube and secured thereto for communication with the interior of the tube through the opening;

a control balloon fixed over an outlet end of the support tube;

a valve opening head secured to the control balloon and to the inflating tube, with a passage therethrough communicating the interior of the control balloon with the inflating tube, said valve opening head having means thereon for opening said outlet valve in response to movement of the valve opening head towards end to end engagement with the outlet end of the support tube; and resilient means connecting the valve opening head to the outlet end of the support tube and biasing the opening head away therefrom.

14. An assembly according to claim 13 wherein the inlet and outlet valves comprise spaced, opposed valve seats in the support tube, respective valve elements engagable with the valve seats to close the tube at respective spaced locations, and resilient means biasing the valve elements in engagement with respective seats.

15. An assembly according to claim 14 wherein the resilient means comprise a single resilient element extending between the valve elements.

16. An assembly according to claim 15 wherein the valve element of the inlet valve comprises a pin projecting through the valve seat in a closed condition of the inlet valve for engagement by a syringe inserted into the adjacent end of the support tube.

17. An assembly according to claim 16 wherein the valve opening head comprises a pin engagable with the valve element of the outlet valve, to lift the outlet valve element from the outlet valve seat in response to movement of the opening head towards the outlet end of the support tube.

* * * * *